(12) United States Patent
Berkson

(10) Patent No.: US 8,703,477 B2
(45) Date of Patent: Apr. 22, 2014

(54) VERMICOMPOSTER APPARATUS AND METHOD

(76) Inventor: Richard L. Berkson, San Anselmo, CA (US)

(*) Notice: Subject to any disclaimer, the term of this patent is extended or adjusted under 35 U.S.C. 154(b) by 211 days.

(21) Appl. No.: 13/373,307

(22) Filed: Nov. 10, 2011

(65) Prior Publication Data

US 2013/0118410 A1 May 16, 2013

(51) Int. Cl.
*C12M 1/00* (2006.01)
*C12M 1/34* (2006.01)
*A01K 29/00* (2006.01)

(52) U.S. Cl.
USPC .............. 435/290.1; 435/290.2; 119/6.7

(58) Field of Classification Search
USPC .......... 435/289.1, 290.1, 290.2, 291.2, 291.3, 435/291.4; 119/6.7
See application file for complete search history.

(56) References Cited

U.S. PATENT DOCUMENTS

| | | | | |
|---|---|---|---|---|
| 6,548,294 | B1* | 4/2003 | Ritter et al. | 435/290.1 |
| 7,879,600 | B2* | 2/2011 | Chee | 435/290.2 |
| 2003/0059931 | A1* | 3/2003 | Gitt | 435/290.1 |
| 2010/0273251 | A1* | 10/2010 | Rhoads et al. | 435/290.1 |
| 2012/0244611 | A1* | 9/2012 | Branham | 435/290.1 |

FOREIGN PATENT DOCUMENTS

CN 1085040 * 9/1992

* cited by examiner

*Primary Examiner* — Michael Hobbs
*Assistant Examiner* — Timothy Barlow
(74) *Attorney, Agent, or Firm* — Henry J. Recla

(57) ABSTRACT

A composting apparatus and composting methods are disclosed. In one embodiment, a composting apparatus includes a housing having walls defining an interior working chamber. The working chamber is separated vertically from a second, lower collection chamber by a grid floor. Immediately below the grid floor is an agitator shaft with perpendicularly disposed agitator arms. Rotation of the agitator shaft extends the agitator arms through the horizontal spaces in the grid floor into the underside of vermicompost material in the working chamber. Horizontal movement of the agitator mechanism disrupts the underside of vermicompost to cause material to fall into a drawer in the lower collection chamber.

11 Claims, 7 Drawing Sheets

VERMICOMPOSTER APPARATUS AND METHOD

CROSS-REFERENCE TO RELATED APPLICATIONS

None.

FEDERALLY SPONSORED RESEARCH

None.

SEQUENCE LISTING

None.

BACKGROUND

Various methods have been developed to utilize earthworms to eat decomposing organic matter and excrete a material known as vermicompost or castings. Vermicompost contains a high concentration of beneficial microorganisms that provide a soil amendment beneficial to the growth of plants. Vermicomposting also reduces the amount of household and commercial food waste that would otherwise make its way into landfills where it decomposes anaerobically and creates greenhouse gases and toxic leachate.

The present invention provides a device which significantly reduces the manual labor required to harvest vermicompost compared to other devices currently available.

One type of vermicomposting device currently available in the market is comprised of a number of stacked pans which, with the exception of the bottom pan, are provided with orifices to allow earthworm migration both up and down between the pans. The bottom pan has a solid floor that collects leachate; the uppermost pan is covered. Initially, a single pan is placed above the bottom pan and bedding, worms and organic matter are added. After the pan is filled with decomposing organic matter, another pan is added on top of the filled pan and the process of adding bedding and organic matter is repeated. The worms can travel from one pan to another via the orifices in the floors of the pans and are always able to reach nutritive matter that is added to the uppermost pan. Periodically the upper pans are unstacked and the vermicompost in the lowermost pan is removed; the removed vermicompost may also contain worms, worm eggs, castings and bedding that must be separated from the vermicompost and returned to the bins. Subsequently this pan is provided with fresh bedding and is replaced in the stack as the top pan to which new nutritive matter is added since the earthworms migrate upwardly to feed and breed and downwardly to deposit eggs. Repeated harvesting of the worms from the converted nutrition and bedding is inconvenient and time consuming in that the job is labor intensive. The pans are very heavy and every pan must be removed to harvest the castings from the lowermost pan. Leachate accumulates in the lowest pan, and frequently clogs the spigot typically used to drain the leachate. If the spigot clogs, the heavy bins must be unstacked in order to drain the bottom pan and remove the accumulated leachate that can produce anaerobic conditions in the bin that can adversely affect the worms and create unpleasant odors.

Another approach is a continuous method in which the worms are fed organic matter above a weight bearing grid. A bar, which rests upon the grid, is pulled across the grid to push the finished vermicompost into a lower collection area. A major problem here is the extreme weight of the organic matter pressing down on the grid making it difficult to manually pull the bar across the top of the grid to force vermicompost through the grid.

Consequently, a need remains for an effective, easy to use apparatus and method for converting organic waste matter into a useful substance and enable harvesting of earthworms when desired. It is desirable that such apparatus be compact, operate virtually continuously while maintaining suitable operating conditions, and enable extraction of vermicompost with unstressful manual effort.

SUMMARY

The present invention provides for the containment of worms in a manner such that they may feed upon organic waste and continuously convert it into vermicompost that can readily be accessed. Several vertically adjacent chambers are defined within a housing. The top chamber of the unit is the working component where worms are seeded at the bottom and organic material is added above for ingestion by the worms. The worms migrate upwardly in the chamber while feeding as more organic material is added, leaving behind their feces known as castings or vermicompost. When the worms are near the top of the chamber, the material at the base consists essentially only of the vermicompost, and new organic material can be overlaid in the working chamber as the conversion takes place. The working chamber includes a floor consisting of parallel members, otherwise known as a grid, that support the bedding and vermicompost. Spacing between the grid floor members allows for periodic scraping of the underside of the vermicompost to disrupt the bottom layer of material and allow castings to drop into a collection chamber. The collection chamber also provides for the collection of liquids generated during the vermicomposting process, also known as "leachate".

An apparatus in accordance with the invention for converting organic waste material into vermicompost in one practical example comprises a housing having walls defining an interior working chamber volume and including apertures in the walls permitting air movement into the interior volume. The housing also includes a lower collection chamber with two floors, the upper floor comprising a transverse wall, or grid, having apertures for allowing liquid to flow down into the lower zone of the collection chamber. This collection chamber may be in the form of a drawer, which can be withdrawn for separation of a high yield casting mix and disposal of leachate. The upper floor of the collection chamber in the preferred embodiment may be removed to facilitate removal of castings and leachate and cleaning of the collection chamber. Immediately above the collection chamber, a single movable element, otherwise known as an agitator assembly, lies horizontally across the collection chamber above. Above the movable element is a floor comprised of a grid consisting of a plurality of parallel members. The movable element is comprised of elements known as agitator arms which lay horizontally but which can be rotated to extend upwards between the horizontal members of the grid floor into the working chamber. When the agitator assembly is moved horizontally and rotated, the agitator arms extend into the vermicompost supported by the floor of the working chamber; the agitator arms are shaped to disrupt the vermicompost. The disrupted vermicompost falls through the spacings between the parallel elements of the working chamber floor into the collection chamber, which may then be pulled out for removal of the vermicompost product. The top of the housing is removable so a new mix of organic material and worms can be added for conversion of the organic material into vermicompost without disrupting other layers or chambers.

An advantageous feature is a movable mechanism, otherwise known as an agitator assembly, which lies below the floor of the working chamber. The floor supports the weight of the vermicompost mass, facilitating the horizontal movement and rotation of the agitator assembly to scrape the bottom layer of vermicompost. Rotation of the agitator assembly can be varied to change the angle and depth of penetration into the vermicompost as necessary for efficient disruption with minimal effort. The agitator assembly only disrupts the lower layer of vermicompost mass to minimize disruption of the worms, and to facilitate a continuous process for reduction of the nutritional matter and reproduction of worms. The floor in one example comprises a number of parallel shafts which define a grid having a plurality of intermediate spacings which retain and support the somewhat self-adherent vermicompost. The shafts are spaced to allow for continuous movement of the agitator assembly across the entire length of the working chamber. The agitator assembly is composed of multiple protruding elements, known as agitator arms, separated by gaps to allow for the rotation of the protruding elements to a position that may range from horizontal to vertical, with the shafts of the floor extending horizontally between the protruding elements without impeding the rotation of the protruding elements or the horizontal movement of the agitator assembly.

If the agitator assembly is rotated ninety degrees from horizontal, the protruding elements will extend vertically upright into the vermicompost supported by the floor above the agitator assembly. A subsequent horizontal movement of the agitator assembly will scrape the vermicompost to a greater depth than would an angle of forty-five degrees from horizontal, but will require more effort. Varying the angle of rotation varies both the effort required and vermicompost removed, and will affect the number of horizontal passes required to scrap the vermicompost. The amount of vermicompost removed can be varied depending on how completely the organic material has been converted to castings.

The invention also comprises a continuous process for reducing organic waste material to useful solid matter using worms. The process includes the steps of disposing a mix of worms and nutritional material in a first zone under aerated conditions, retaining the mix in the first zone until ingestion by the worms during upward migration through the bedding has built up an at least partially self-adhered layer of castings, breaking up or fragmenting a part of the casting layer, dropping the castings into a collection chamber, periodically withdrawing castings, and periodically adding new bedding material at the top to continue to facilitate reduction of organic waste material.

GENERAL DESCRIPTION OF THE DRAWINGS

DETAILED DESCRIPTION

Figure 1:
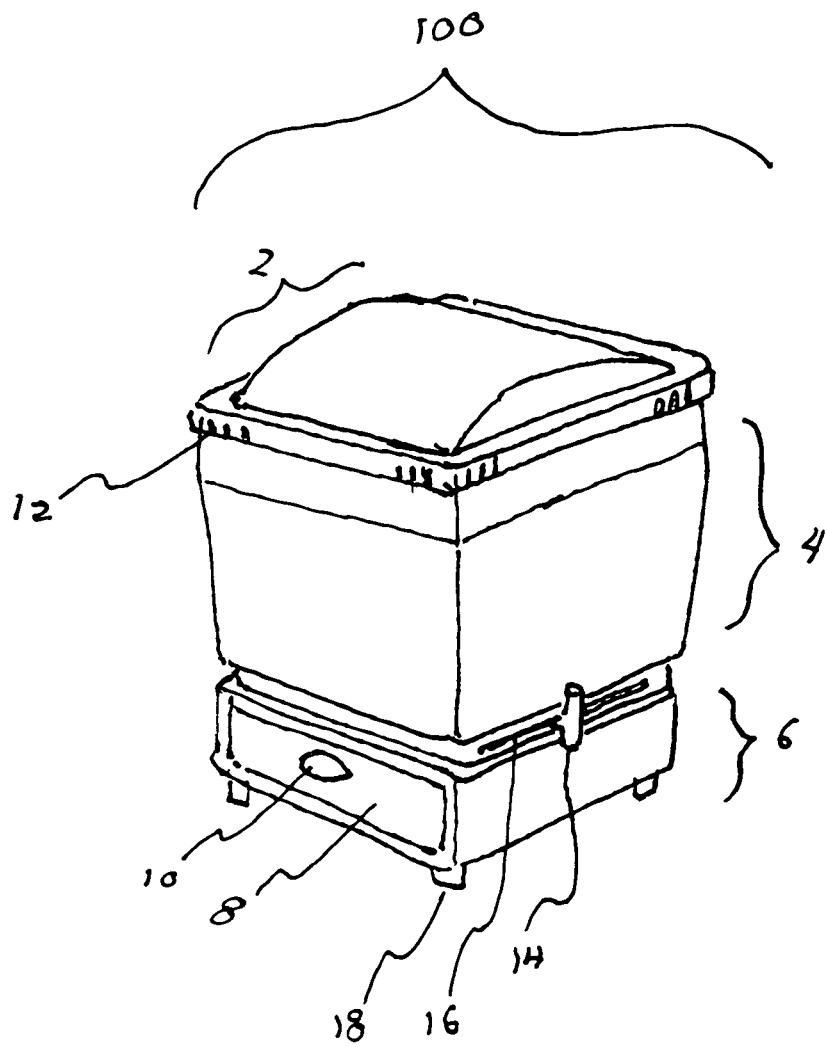
FIG. 1 is a perspective view of the invention.
Figure 5:
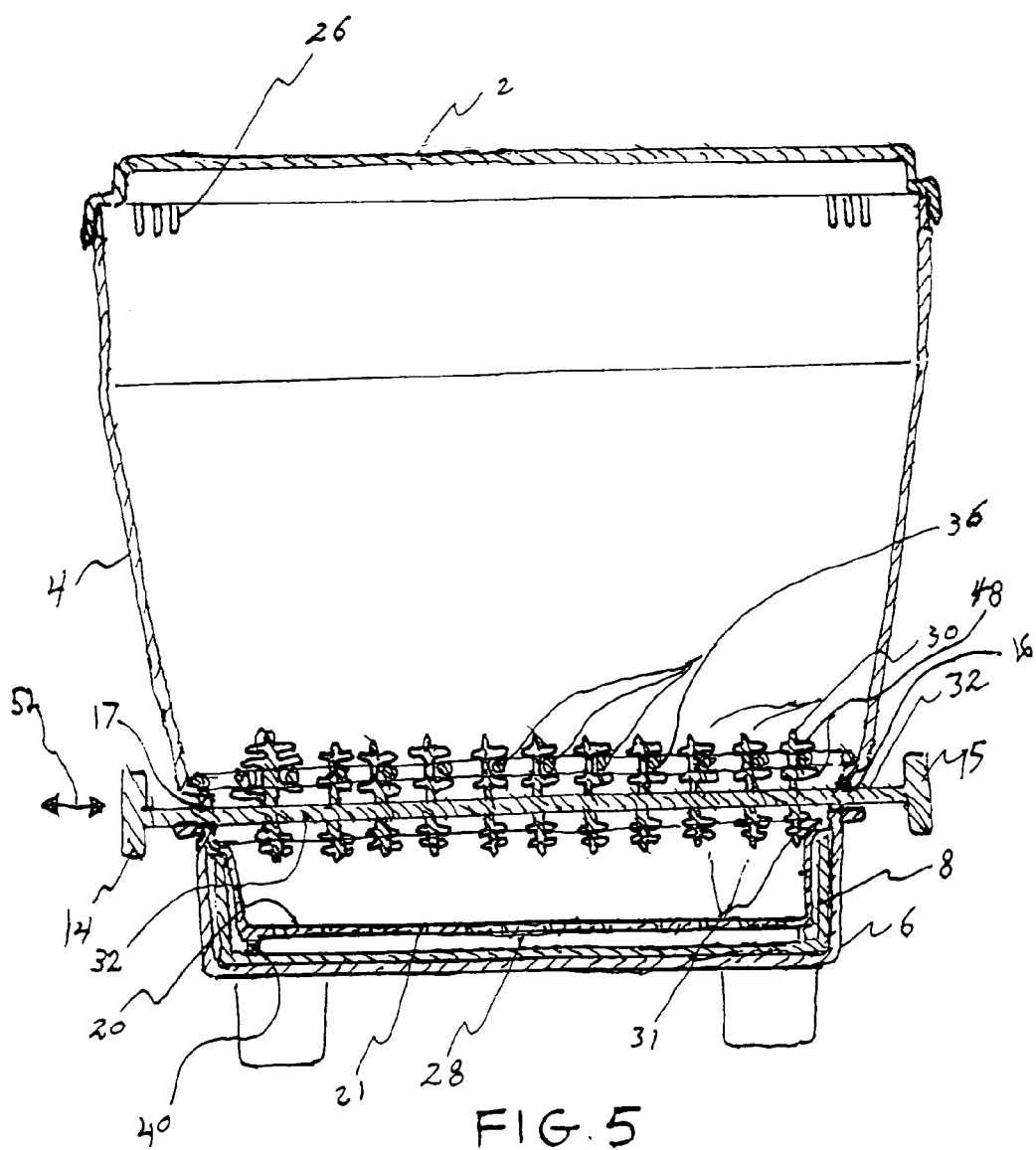
FIG. 5 is a section view of the invention.

An apparatus in accordance with the present invention 100 as shown in FIG. 1 includes a main bin, otherwise known as a working chamber 4 which holds the worms and food, a collection chamber 6 for the collection of the castings, and a lower zone 28, shown in the section view in FIG. 5, for the collection of liquid. Bedding for the worms composed of a carbon-based material such as shredded newspaper, shredded coconut husk or cornhusk, or peat moss is placed on the grid 36 of the working chamber 4 as shown in the section view in FIG. 5. Organic material such as food waste is then added along with a quantity of worms and placed in working chamber 4. The worms consume the organic material, and the bedding, migrating upwardly as they do so, and lay their feces called castings in the material, or vermicompost. More organic material is added at the upper region of the chamber by opening hinged 22 lid 2, shown in FIG. 2, and adding material as the previous material is consumed and/or removed. After a period of time, the bottom layers of the chamber will consist of the worms' vermicompost, a well-known soil amendment. Since it is organically produced, the vermicompost can be used as a soil amendment for extended periods of time without imposing any of the adverse effects typically caused by chemical fertilizers. The minimum size of said bin 4 is twelve inches by twelve inches by approximately fourteen inches deep.

Figure 2:
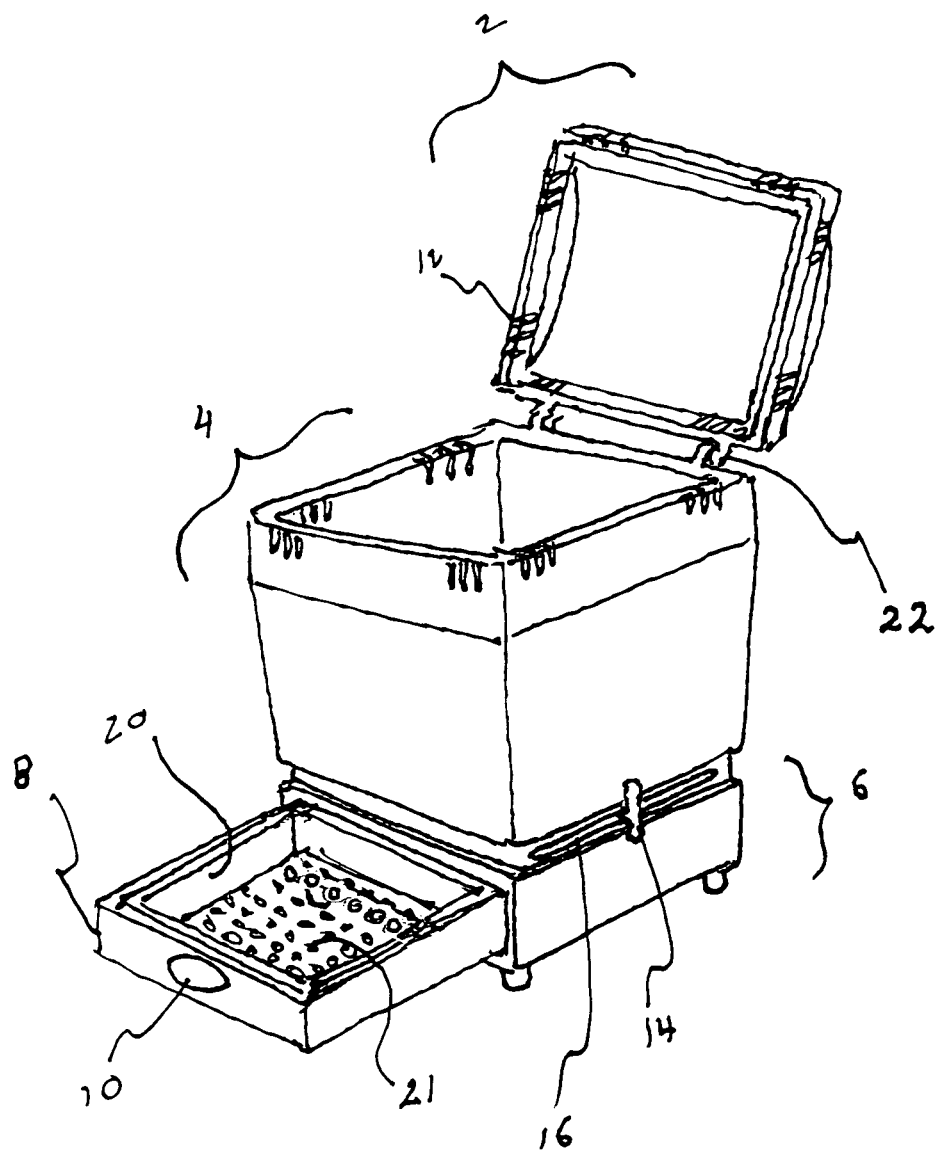
FIG. 2 is a perspective view of the invention with the lid lifted and drawer opened.

The resulting lower level of vermicompost sits on the top of grid portion 36, as shown in the section view in FIG. 5, and can be induced to fall into the drawer 8 area of the collection chamber 6 when a user slides the handles 14, 15 which move an attached agitator shaft 32 shown in the section view in FIG. 5. The agitator shaft 32 causes a plurality of attached agitator arms 30, 31 to comb the lowest level of vermicompost causing it to drop into a tray 20, shown inside drawer 8 as illustrated in FIG. 2. Tray 20 includes a plurality of apertures 21 which allow excess moisture to fall to the space between the tray 20 floor and the base of the collection chamber 6 as shown in the section view in FIG. 5. The base of removable tray 20 includes standoff feet 40 which create the space 28 for moisture to collect. The agitator shaft 32 exits either side of main bin 4 through slots 16, 17 as shown in the section view in FIG. 5. Bottom legs 18 help keep the entire assembly 100 off the ground or table top. Optionally, leg extensions can be added to existing legs 18 to allow the current table top unit 100 to be a floor model without the need of a separate table.

Figure 3:
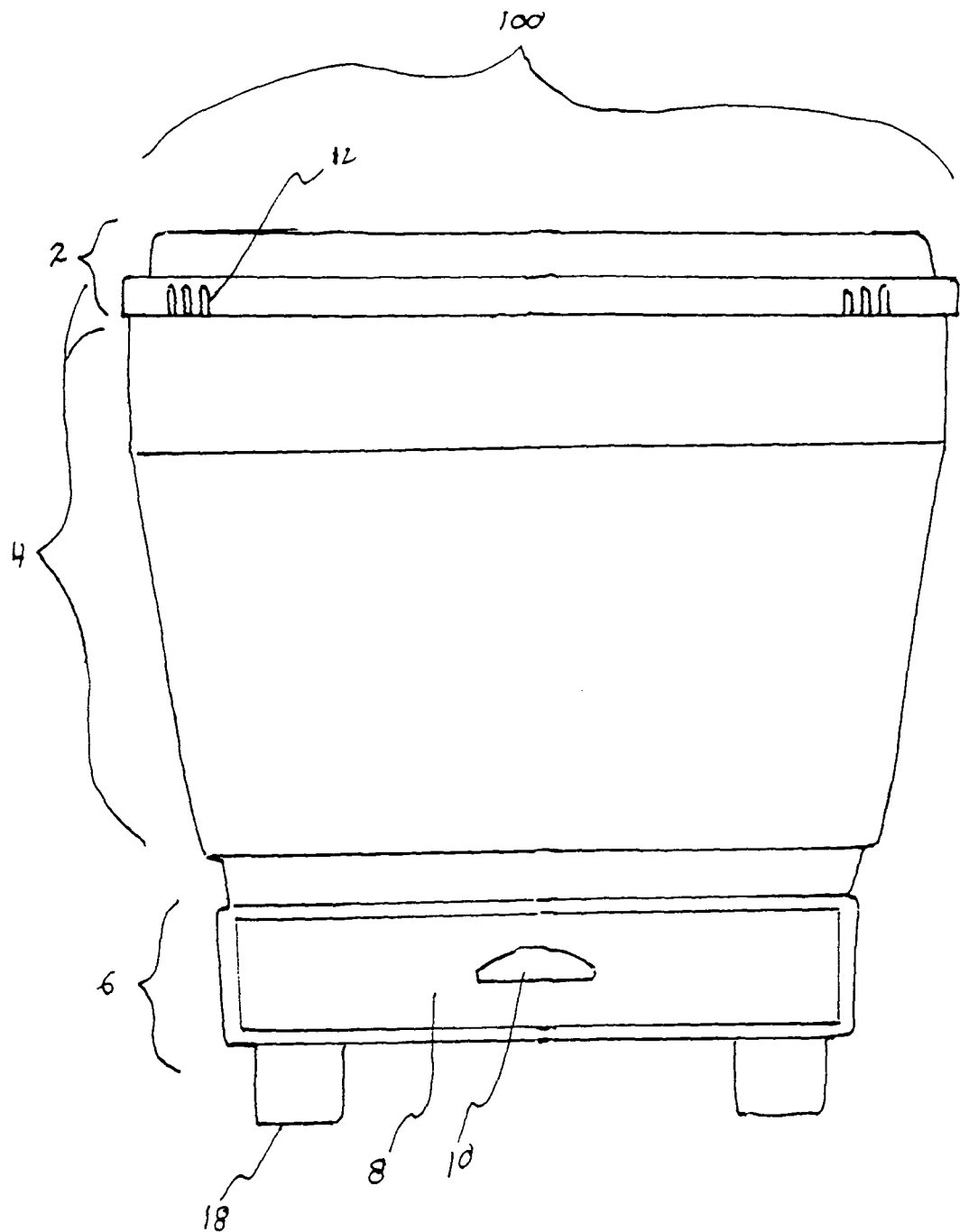
FIG. 3 is a front plan view of the invention.

FIG. 3 shows a front view of the invention 100. Drawer handle 10 is fixed to the front of drawer 8 and allows easy pulling out of the drawer 8. Slots 12 are found on all corners of lid 2 and correspond with the slots 26 in the top of bin area 4 as shown in the section view in FIG. 5. These slots 12, 26 are approximately one sixteenth of an inch in width, which is thin enough so that worms cannot get through. The slots provide needed air flow for the optimal conditioning of the contents within the bin 4.

Figure 4:
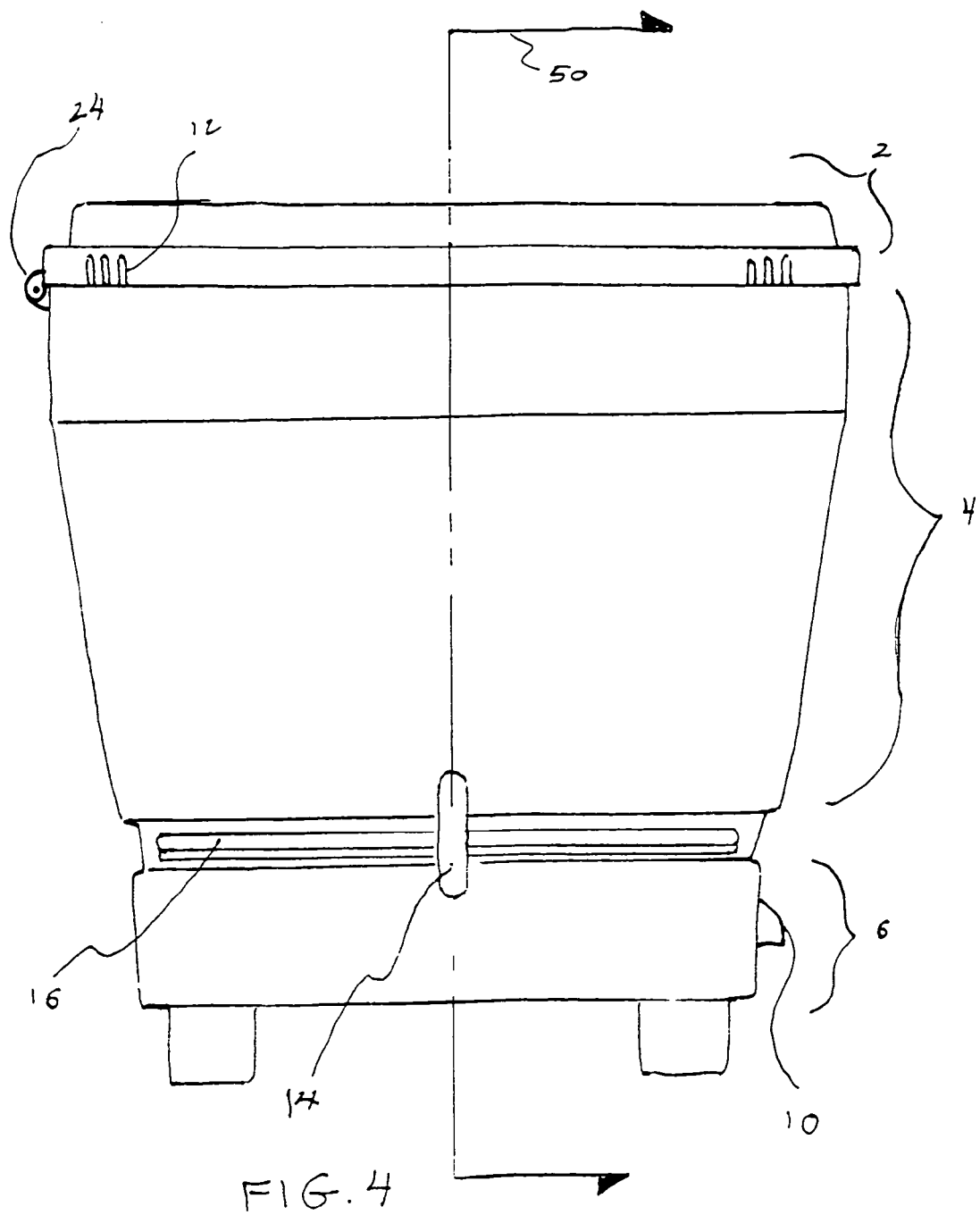
FIG. 4 is a side plan view of the invention.

FIG. 4 is a side view of the invention 100. Hinge member 24 can be seen which attaches the lid portion 2 to the main bin portion 4. Slot 16 can be clearly seen which allow for the sliding of the agitator shaft 32. Section line 50 defines the section view shown in FIG. 5.

Referring to FIG. 5, Agitator shaft 32 is shown exiting slots 16, 17. Attached agitator arms 30, 31 each include attached disk shapes 48 that can help clean the rods of the grid 36 when the user slides the agitator shaft 32 back and forth. The user can slide the shaft 32 left and right, as shown by direction arrow 52, so that the disks 48 can clean the left side of the grid rods 36 when the shaft 32 is moved to the left and the right side of the grid rods 36 when the shaft 32 is moved to the right. Horizontal disk members 48 are perpendicularly attached to each agitator arm 30, 31 which help clean each rod 34 of the grid assembly 36. In the preferred embodiment, the disk members are actually helical in shape. Additionally, in the preferred embodiment, a flexible curtain member covers each slot 16, 17 thereby helping reduce the chance of vermicompost or worms to accidentally exit the slots 16, 17.

Figure 6:
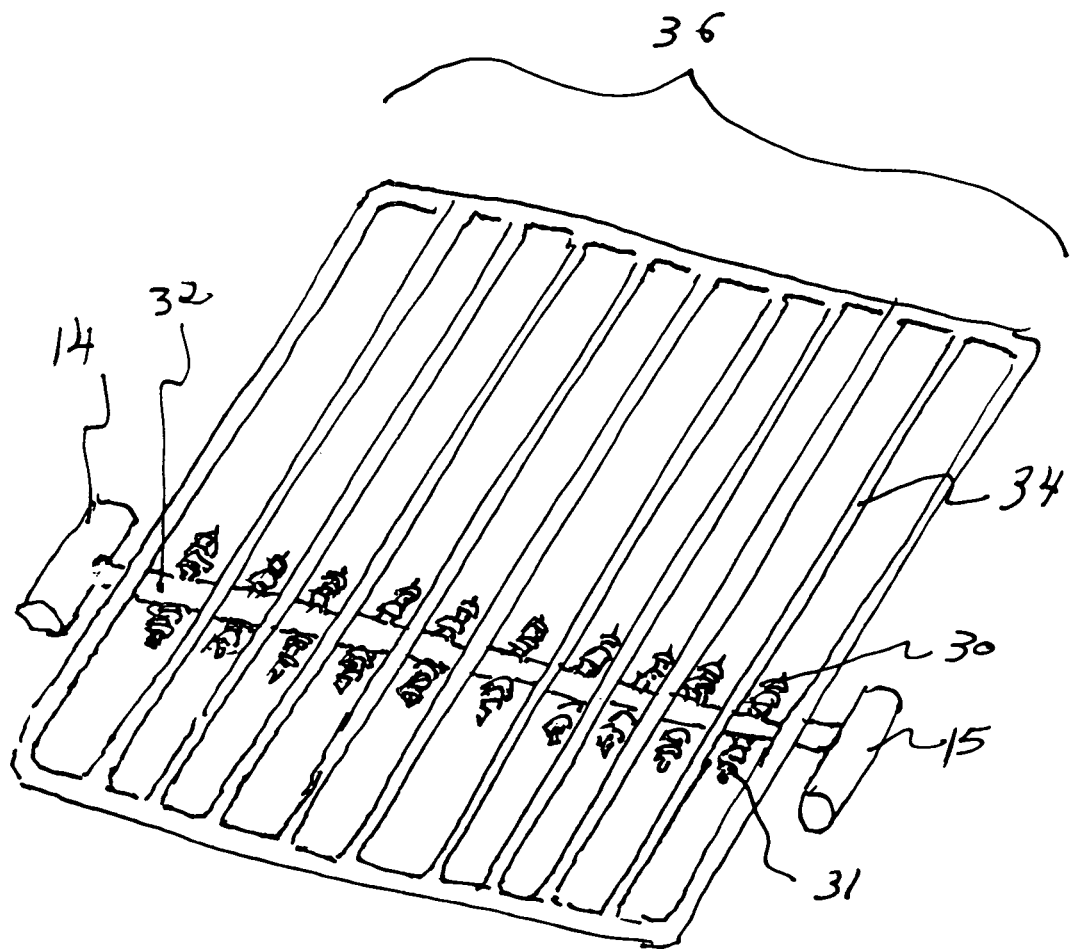
FIG. 6 is a perspective view of the grid and agitator with agitator extension arms in the horizontal position.
Figure 7:
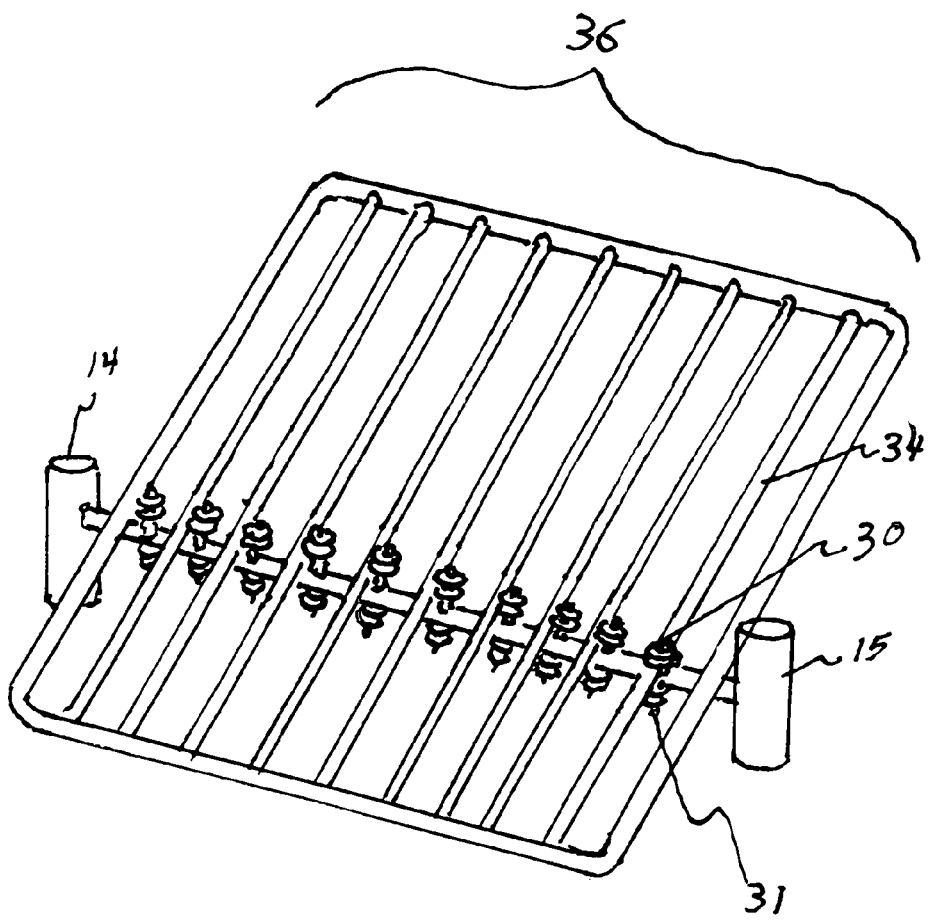
FIG. 7 is a perspective view of the grid and agitator with the agitator extension arms in the vertical position.

FIG. 6 shows a perspective view of the grid 36 and the agitator assembly which includes handles 14. 15, shaft 32 and agitator arms 30, 31. In this view, the arms 30, 31 are parallel with each rod 34 of the grid assembly 36. This orientation allows that user to slide the shaft 32 easily because the arms 30, 31 are not in complete contact with the vermicompost located above the grid 36. The user can then decide what angle to orient the arms 30, 31 by rotating the handles 14, 15 from parallel to the grid 36 all the way to perpendicular to the grid 36 as shown in FIG. 7. The ability to slide the shaft 32 left and right as well as forward and backward gives the user maximum ability to gather and release processed vermicompost so that it drops into the tray 20 directly below the grid 36. As vermicompost is dropped into the tray 20, it makes room for additional food scraps to be added to the top of the bin 4.

Operation

To begin, a mix of worms and food or bedding material is placed into the top portion of the bin 100. Initially, the mix sits atop a temporary decomposable barrier that has been set flat upon the grid 36. For the initial seeding of the worms, a biodegradable material such as paper or cardboard is placed over the grid 36 to prevent the worms and loose organic material from falling through before the self-adherent vermicompost mass has an opportunity to accumulate. Before the time it is necessary to remove castings, typically within one to two months, this biodegradable material will have begun to decompose or fallen into the collection tray 20.

As the worms eat their way upward, a layer of vermicompost, which is somewhat self-adherent but not hard or resilient in character, forms above the grid. Once sufficient time has elapsed, and the temporary barrier has deteriorated, the handle 14, 15 can be rotated and moved horizontally, thereby activating the agitator shaft 32 and attached agitator arms 30, 31. The rotation of the agitator arms 30, 31 engages the underside of the vermicompost layer, and fragments fall through the gaps in the grid 36 into the collector tray 20. Collected vermicompost, which contains moisture, drains its liquids through a plurality of drain apertures 21 in the tray 20 into a lower liquid collection zone 28. Once liquids have accumulated, the drawer 8 can be removed to pour out the liquid. The mass of matter in the working chamber 4 above the grid floor 36 shifts down so that the upper part of the bin 4 can receive new organic matter.

Typically, castings initially are removed after a period of about thirty days while additional food is added about every one to seven days. After the initial thirty days, the castings and liquid may be removed weekly or more often, depending on the activity of the worms and amount and type of food added.

The separation of the liquid prevents drowning of the worms if they fall into the tray 20. The liquid also maintains moist conditions in the unit, the worms preferring an eighty to ninety humidity factor. In hot, dry climates, for example, water can be added to the working chamber to boost humidity and to promote evaporative cooling. Typically, however, moisture is not a problem as the worm's food, the organic compost material, contains substantial liquid.

The worms require a temperature that is between about thirty-two and about one hundred and ten degrees F. Preferably, the temperature is about seventy degrees F. To prevent overheating the unit should be kept in the shade, as provided by natural vegetation or an overhanging cover, not shown. During high temperatures, additional moisture can be added which will evaporate and aid in cooling. During cold temperatures, the unit must be kept from freezing or the worms will die. The worms can tolerate temperatures near but above freezing, but as cold-blooded creatures, their metabolism will slow down accordingly.

Once a portion of the vermicompost has been removed, additional fresh food or other organic matter can be added to the top of the bin 4 after opening the lid 2. As the worms migrate upwardly into the new nutrient matter, they deposit eggs that mature in a normal cycle to replenish and expand the worm population. The lowermost portion of matter in the working chamber is efficiently converted to vermicompost, in an essentially continuous manner. It can be seen that, once started, no special complex or laborious activities are required thereafter to replenish the feed materials and extract the converted product. This process is commonly known as "continuous flow", as it does not require the periodic manual separation and extraction of worms and vermicompost from multiple stacked bins.

This process can continue indefinitely, and worms can be harvested at the top of the working chamber if an overpopulation of worms exists.

The invention claimed is:

1. An apparatus for converting organic waste material into vermicompost using worms, said apparatus comprising:
   an upper section and a lower section connected to said upper section;
   said upper section having contiguous front, back and side walls with an open bottom enclosing an interior volume defining an organic waste material and worm receptacle, wherein said organic waste is converted to vermicompost by ingestion in the worms;
   said upper section front, back and side walls terminating in an upper peripheral edge defining an open top;
   said upper section front, back and side walls including aeration ports extending therethrough;
   said open bottom of said upper section having a predetermined cross-sectional area, a grid comprising a matrix of parallel spaced rods lying in a plane and having a cross-sectional area approximately equal to said predetermined cross-sectional area of said open bottom, said grid being mounted to said side walls of said upper section and extending across said bottom of said interior volume, said rods extending parallel to said side walls of said upper section, wherein said front, back and side walls of said upper section together with said grid define said organic waste material and worm receptacle,
   a lid removably mounted over said upper section open top and overlapping said peripheral edge;
   said lower section having contiguous front, back and side walls with an open top, said open top having a cross-sectional area approximately equal to said predetermined cross-sectional area of said open bottom, said front wall of said lower section including an opening, said opening together with said side walls of said lower section defining a channel extending into said lower section, said channel having a cross-sectional area approximately equal to said predetermined cross-sectional area of said open top;
   a drawer having a bottom and side walls, said drawer slidably mounted in said channel and disposed in said lower section to underlie said grid, said drawer being slidably removable from said lower section;
   said side walls of said lower section having opposing slots extending therethrough and disposed parallel to said parallel rods of said grid, said opposing slots in said side walls positioned above said drawer slidably mounted in said channel and adjacent said grid;

an agitator assembly comprising a shaft extending through said slots in said side walls of said lower section, said shaft having opposing ends extending laterally from said side walls to define handles for sliding said shaft along said slots and laterally of said slots and for rotating said shaft within said slots;

said shaft further including a plurality of agitator arms extending perpendicular therefrom and spaced thereon approximately equal to said spaced parallel rods of said grid, said agitator arms each having a length such that they rotate between said rods when said shaft is rotated along said slots and as said shaft is slid along said slots, and said arms move laterally between said rods as said shaft is slid laterally of said slots; and whereby said movement of said agitator assembly decouples vermicompost from said rods and just above said grid permitting said vermicompost to fall into said drawer.

2. An apparatus as claimed in claim 1, wherein said upper and lower section are a monolithic structure.

3. An apparatus as claimed in claim 1, wherein said agitator arms further include laterally extending members for decoupling vermicompost above and below said rods.

4. An apparatus as claimed in claim 3, wherein said laterally extending members are disc-shaped.

5. An apparatus as claimed in claim 3, wherein said laterally extending members are helical-shaped.

6. An apparatus as claimed in claim 1, wherein said lid is hinged to said back wall of said peripheral edge of said upper section.

7. An apparatus as claimed in claim 1, wherein said drawer is lined with a perforated tray for collecting vermicompost and allowing liquid to drain from collected vermicompost.

8. An apparatus as claimed in claim 1, wherein said opposing slots are covered with curtains to deter worms or vermicompost from exiting through said slots.

9. An apparatus as claimed in claim 2, wherein said lower section further includes a bottom surface integral with said front, back and side wall of said lower section and defining the bottom of said channel.

10. A process of reducing organic waste material to useful solid and liquid matter using worms, the process comprising;
providing an apparatus as defined in claim 1;
disposing a mixture of worms and organic waste material in said upper section with said worms disposed toward the bottom;
maintaining said mixture in said upper section under aerated conditions;
retaining the mixture in said upper section until said organic waste is ingested by the worms during their upward migration through the waste material and a layer of vermicompost is formed adjacent the grid;
activating the agitator assembly by rotating and sliding movement of the shaft to decouple vermicompost from and just above the grid with said arms thereby permitting the decoupled vermicompost to fall into the drawer; and
removing the drawer from the lower section and collecting the vermicompost from the drawer.

11. A process of reducing organic waste material to useful solid and liquid matter using worms as claimed in claim 10, and further lining said drawer with a perforated tray for collecting vermicompost and allowing liquid to drain from collected vermicompost.

\* \* \* \* \*